United States Patent [19]

Grimmer et al.

[11] Patent Number: 5,017,700
[45] Date of Patent: May 21, 1991

[54] PREPARATION OF RIBOFLAVIN-5'-PHOSPHATE (5'-FMN) AND ITS SODIUM SALT, AND OF RIBOFLAVIN-4',5'-CYCLOPHOSPHORIC ACID ESTER CHLORIDE AS AN INTERMEDIATE

[75] Inventors: Johannes Grimmer, Ludwigshafen; Hans Kiefer, Wachenheim, both of Fed. Rep. of Germany

[73] Assignee: BASF Aktiengesellschaft, Ludwigshafen, Fed. Rep. of Germany

[21] Appl. No.: 413,590

[22] Filed: Sep. 28, 1989

[30] Foreign Application Priority Data

Oct. 19, 1988 [DE] Fed. Rep. of Germany ....... 3835563

[51] Int. Cl.$^5$ .......................... C07F 9/02; C07F 9/14; C07D 475/14
[52] U.S. Cl. .................................. 544/244; 544/250; 544/251; 558/84
[58] Field of Search ....................... 544/250, 251, 244; 558/84

[56] References Cited

U.S. PATENT DOCUMENTS 1,684,738 12/1923 Marschalk ............................ 558/84
2,111,491 3/1938 Kuhn et al. ......................... 544/251
2,610,177 9/1952 Flexser et al. ...................... 544/251
2,661,365 12/1953 Gaurath et al. ...................... 558/84

FOREIGN PATENT DOCUMENTS 1007363 7/1985 U.S.S.R. .

OTHER PUBLICATIONS

Hutchinson "Organophosphorus Chemistry", p. 141, Burlington House, London, 1982.

Siderenko, "Synthesis of ——— ", CA 88: 136229j (1978).
Chemical Abstracts, vol. 83 (1975), p. 695, 79549f, 79550z, and 79551a.

Primary Examiner—Frederick E. Waddell
Assistant Examiner—Celia Chang
Attorney, Agent, or Firm—Oblon, Spivak, McClelland, Maier & Neustadt

[57] ABSTRACT

Riboflavin-4',5'-cyclophosphoric acid chloride of the formula I

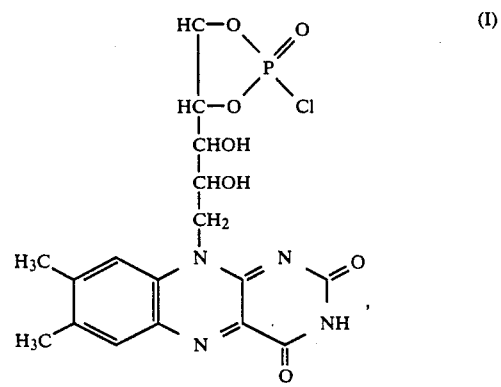

its preparation by reacting an alkali metal salt of riboflavin, in an aprotic solvent, with phosphorus oxychloride, its use for the preparation of riboflavin-5'-phosphate and of the sodium salt of riboflavin-5'-phosphate, and a process for the preparation of riboflavin-5'-phosphate or its sodium salt via the novel phosphoric acid ester chloride.

1 Claim, No Drawings

PREPARATION OF RIBOFLAVIN-5'-PHOSPHATE (5'-FMN) AND ITS SODIUM SALT, AND OF RIBOFLAVIN-4',5'-CYCLOPHOSPHORIC ACID ESTER CHLORIDE AS AN INTERMEDIATE

The present invention relates to riboflavin-4',-5'-cyclophosphoric acid ester chloride of the formula I

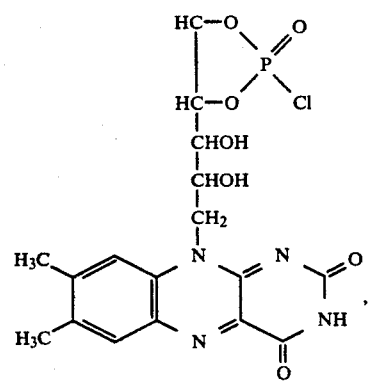

and to a process for the preparation of riboflavin-5'-phosphate (5'-flavin-mononucleotide and hence hereinafter referred to as 5'-FMN) and for the preparation of the commercial monosodium salt of 5'-FMN via the novel ester chloride of the formula I.

5'-FMN is a compound which plays an important role as a coenzyme in various enzymatic reactions in a living organism and which is therefore used in the form of its salts, especially in the form of sodium 5'-FMN, as an additive for medicaments, foodstuffs and feeds. Sodium 5'-FMN is also used as a starting material for flavinadenine dinucleotide, which is used as a therapeutic agent to combat vitamin $B_2$ deficiency.

Industrially, sodium 5'-FMN is generally obtained by direct reaction of riboflavin with a phosphorylating agent, such as partially hydrolyzed phosphorus oxychloride, followed by treatment of the resulting 5'-FMN with sodium hydroxide solution. The selective phosphorylation of riboflavin is not entirely straightforward. Thus, for example, according to U.S. Pat. No. 2,610,177, a large excess of phosphorus oxychloride is used. According to C.A. 83 (1975), 7955ia, C.A. 83 (1975), 79549f (Japanese Preliminary Published Application 50/25 597) and C.A. 83 (1975), 79550z (Japanese Preliminary Published Application 50/25 598), a slight excess of phosphorus oxychloride in a solvent such as tetrahydrofuran, diethylene glycol dimethyl ether, monoethylene glycol dimethyl ether, triethyl phosphate, 1,2-dichloroethane or 1,2-dibromoethane is recommended. On repeating the examples we have found that under the stated conditions no 5'-FMN at all was formed in many cases, whilst in others only extremely small amounts of 5'-FMN were obtainable. The high yields quoted in loc. cit. are presumably due to analytical problems.

In certain cases, the phosphorylation is carried out in the presence of pyridine (cf. U.S. Pat. No. 2,111,491) or in the presence of acetonitrile (cf. Techn. Rapport No. 2715 (1979) by Frantz Kaufmann of Grindstedt Verket, Denmark).

In all the known processes of preparation, a crude product which still contains substantial amounts of unconverted riboflavin as well as isomeric monophosphates and polyphosphates as byproducts is initially obtained. Hence, the 5'-FMN must be subjected to a technically complicated purification procedure, to give products which conform to the purity criteria of the U.S. and European pharmacopeia. For example, Chemical Engineering, Nov. 1954, pages 120 et seq. discloses that in one production process the 5'-FMN is concentrated by dissolving the isomer mixture in the form of monoammonium salts by repeated treatment with ethanolamine, and separating this solution from unconverted and undissolved riboflavin.

The involved process steps and, in addition, the use of large amounts of phosphorus oxychloride relative to the riboflavin (vitamin $B_2$) to be phosphorylated themselves show that such processes can represent a not insignificant effect on the chloride pollution of the effluent. The purification processes for vitamin $B_2$ phosphate by absorption on a cellulose ion exchanger and elution with a sodium oxalate/oxalic acid buffer or ammonium formate/formic acid buffer (cf. Japanese Published Application 47/8836 and Japanese Published Application 47/8554) also do not make the process more economical and more environment-friendly, since, in industrial applications, excessively large amounts of buffer salts are employed.

We have now found that, surprisingly, salts of 5'-FMN are obtained particularly advantageously if, contrary to the prior art, it is not the free riboflavin, but its metal salts, preferably the alkali metal salts, especially the potassium salt (II) of riboflavin which are employed for the phosphorylation. This first results in the riboflavin-4',5'-cyclophosphoric acid ester chloride of the formula I, which to the best of our knowledge has not previously been described in the literature, and which can be separated off in a crystallized form. This compound can then be hydrolyzed, with ring cleavage, under suitable conditions, and be converted, by partial neutralization with sodium hydroxide solution at pH 5.5, into the sodium salt of 5'-FMN.

If the potassium salt is used, the reaction takes place in accordance with the following equation:

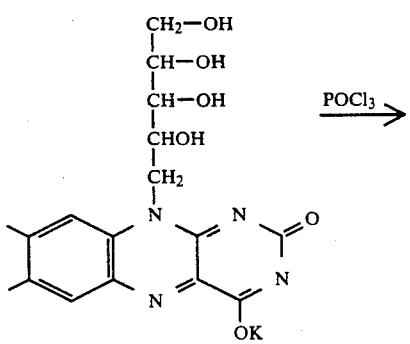

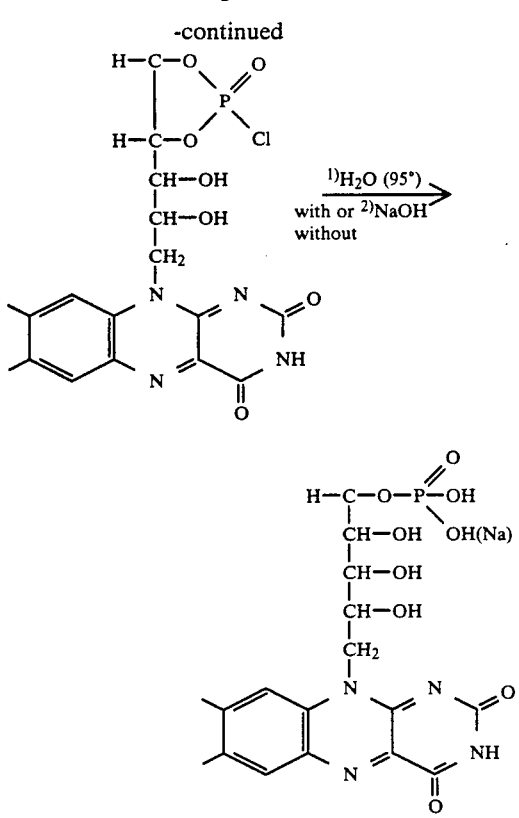

It was very surprising in the reaction of the alkali metal salts of riboflavin with phosphorus oxychloride or with an ester of phosphorus oxydichloride that the attack of the phosphorylating agent should occur in the 4',5'-position of the ribityl residue. It is known from the literature that the negative charge in the anion of riboflavin is localized in the heterocyclic rings, so that anyone skilled in the art would have expected the attack of the phosphorylating agent to take place at the position of highest charge density, namely in positions and 5 of the isoalloxazine ring and not at the remote 4',5'-position of the ribityl residue.

Accordingly, the present invention not only relates to the riboflavin-4',5'-cyclophosphoric acid ester chloride of the formula I but also to a process for its preparation, wherein an alkali metal salt, especially the potassium salt, of riboflavin is reacted in a suitable aprotic solvent, at from 20° to 50° C., preferably at about 30°-45° C., with from 1.2 to 3 moles of phosphorus oxychloride per mole of the alkali metal salt, and, where appropriate, the product which crystallizes out of the reaction mixture is isolated by filtration.

Suitable aprotic solvents for the reaction are, in particular, linear or cyclic ethers, such as monoethylene glycol dimethyl ether, diethylene glycol dimethyl ether, triethylene glycol dimethyl ether, tetrahydrofuran or dioxane.

The alkali metal salt used as the starting compound is obtained in a simple manner by dissolving the riboflavin in an equimolar amount of a dilute aqueous alkali metal hydroxide solution and causing the resulting salt to crystallize by dropwise addition of methanol. Filtration, washing with methanol and drying gives the alkali metal salt in almost quantitative yield. In the dried state, the alkali metal salt contains one molecule of water of crystallization and is just as stable as riboflavin itself.

It is particularly advantageous to carry out the preparation of the phosphoric acid ester chloride of the formula I by introducing the alkali metal salt of riboflavin into a solution of about 2.8 moles of phosphorus oxychloride per mole of alkali metal salt (i.e. an approximately 1.8 molar excess) in a suitable aprotic solvent. After 2 hours' reaction at 40°-45° C., more than 95% conversion has already been achieved. The crystalline riboflavin-4',5'-cyclophosphoric acid ester chloride formed can be isolated by filtration, or can be immediately hydrolyzed and isomerized to the desired 5'-FMN by adding water to the reaction mixture and heating the batch. The resulting 5'-FMN can then, if desired, be converted to the monosodium salt of 5'-FMN by partial neutralization.

An intermediate isolation of the 5'-FMN is mostly unnecessary, since the sodium salt of 5'-FMN is obtained in the desired purity in a single process step by partial neutralization of the free acid.

Accordingly, the present invention also relates to the use of riboflavin-4',5'-cyclophosphoric acid ester chloride of the formula I for the preparation of 5'-FMN by hydrolysis and isomerization, and to the preparation of the monosodium salt of 5'-FMN by hydrolysis, isomerization and partial neutralization.

The invention further relates to the process described above, wherein, in order to prepare 5'-FMN or its sodium salt, the riboflavin-4',5'-cyclophosphoric acid ester chloride obtained, of the formula I, (a) is hydrolyzed to give riboflavin-4',5'-phosphoric acid ester which
(b) is isomerized to give 5'-FMN and this
(c) is reacted, if desired, with sodium hydroxide to give the monosodium salt of 5'-FMN.

To carry out this process, the procedure followed is generally that to the reaction mixture containing the riboflavin-4',5'-phosphoric acid ester chloride of the formula I (a) there are rapidly added from 30 to 50, preferably from 32 to 35, moles of water per mole of phosphoric acid ester chloride, in the course of which the temperature rises to above 90° C. and riboflavin4',5'-phosphoric acid ester is formed by hydrolysis,
(b) the reaction mixture is kept for a further 5-15, preferably 8-12, minutes at from 80° to 100° C., preferably from 85° to 90° C., by introducing steam, in the course of which the riboflavin-4',5'-phosphoric acid ester formed is essentially isomerized to 5'-FMN,
(c) the isomerization is interrupted by addition of 68-100 moles of water to the reaction mixture and by the cooling which this causes, and,
(d) if desired, for the preparation of the monosodium salt of 5'-FMN, the reaction mixture is brought to a pH of from 5.5 to 6 by means of sodium hydroxide.

If isolated riboflavin-4',5'-cyclophosphoric acid ester chloride is used as starting compound, it is necessary (a) to introduce the latter into an amount of water, heated to 80°-95° C., which suffices to effect dissolution,
(b) to keep the reaction mixture for a further 5-15 minutes at 80-100° C. by introducing steam, to stop the isomerization by subsequent addition of 68-100 moles of water and,
(d) if the preparation of the monosodium salt of 5'-FMN is desired, to bring the reaction mixture to a pH of 5.5-6 with sodium hydroxide.

In the preparation, according to the invention, of 5'-FMN or of its monosodium salt it is necessary to ensure that the reaction mixture containing the riboflavin-4',5'-cyclophosphoric acid ester chloride reaches 80°–100° C. as rapidly as possible and that it is kept at this temperature for the stated time, without intermediate cooling, since otherwise a product with unacceptably high riboflavin content is obtained.

The reaction of the riboflavin-5'-phosphate with NaOH to give its monosodium salt is in general carried out at from 20° to 50° C., preferably at from 30° to 40° C.

The invention further relates to the overall resulting elegant one-vessel process for the preparation 5 of pure riboflavin-5'-phosphate or of its monosodium salt, wherein
(A) an alkali metal salt of riboflavin in a suitable aprotic solvent is reacted, at from 20° to 50° C., with from 1.2 to 3 moles of phosphorus oxychloride per mole of the alkali metal salt,
(B) to the reaction mixture thus obtained, which contains the novel riboflavin-4',5'-cyclophosphoric acid ester chloride of the formula I, there are rapidly added from 30 to 50 moles of water per mole of ester chloride, in the course of which the temperature rises to above 90° C.,
(C) the reaction mixture is kept at from 80° to 100° C. for a further 5–15 minutes by introducing steam,
(D) thereafter from 68 to 100 moles of water are added to the reaction mixture and the riboflavin-5'-phosphate which crystallizes out is isolated, or, if desired,
(E) the reaction mixture obtained according to (D) is brought, at from 20° to 50° C., preferably from 30° to 40° C., to a pH of from 5.5 to 6 by means of NaOH and the monosodium salt of riboflavin-5'-phosphate which crystallizes out, is isolated.

The riboflavin-5'-phosphate obtained in the process according to the invention in general contains less than 6% of riboflavin and from 75 to 80% of riboflavin-5'-phosphate and accordingly conforms to the purity requirements which apply in the pharmaceutical sector. Subsequent expensive purification operations are unnecessary.

The riboflavin-4',5'-cyclophosphoric acid ester chloride of the formula I is a simply obtainable intermediate which offers a simple route to obtaining the desired product 5'-FMN, and its monosodium salt, in high purity.

EXAMPLE 1

Preparation of riboflavin-4',5'-cyclophosphoric acid ester chloride 60.12 g (0.392 mol) of phosphorus oxychloride were introduced into 180 ml of diethylene glycol dimethyl ether and 60 g (0.139 mol) of riboflavin potassium salt, in the form of fine powder, were added in portions, with stirring, during which the temperature rose to 30° C. The reaction mixture was then heated to 45° C. and stirred at that temperature for 2 hours. When the suspension had cooled to room temperature (RT), the product was filtered off with suction, under nitrogen, then washed with diethylene glycol dimethyl ether and subsequently with acetone, and finally dried under reduced pressure.

The yield was 62.0 g, corresponding to 97.8% of theory. Analysis:

Content of cyclic chloride, according to HPLC: 95%
The molecule ion was measured by means of the FAB-MS method (cf. K. L. Rinehart in Science 218 (1982), 254).
The molecular weight determination gave a figure of 456 g/mol, which corresponds to the title compound
The product still contained potassium salts.

EXAMPLE 2

Preparation of riboflavin-5'-phosphate 60 g (0.139 mol) of riboflavin potassium salt, as a fine powder, were introduced in portions into a mixture of 180 ml of diethylene glycol dimethyl ether and 60.12 g (0.392 mol)=36 ml of phosphorus oxychloride, and thereafter the reaction mixture was stirred for 2 hours at 45° C. 75 g of water were then added rapidly at the same temperature, whereupon the temperature rapidly rose to 90°–95° C. It was kept at this value for from 10 to 15 minutes by introducing steam. During the subsequent dropwise addition of 170 ml of water, the reaction mixture was cooled slowly, in the course of which riboflavin-5'-phosphate began to precipitate as early as from 70° to 80° C. After a final stirring period of 2 hours at 20°–25° C., the product was filtered off with suction and the residue was washed first with a water/ethanol mixture (50:50 by volume) and then with a small amount of pure ethanol, and was subsequently dried at 75° C. under reduced pressure.

The yield was about 52 g corresponding to 82.0% of theory. Analysis: According to HPLC the product contained about 75–78% of riboflavin-5'-phosphate, about 9–11% of riboflavin-4'-phosphate, about 5–7% of riboflavin-3'-phosphate and about 4–6% of free riboflavin.

EXAMPLE 3

Preparation of the sodium salt of riboflavin-5'-phosphate

The procedure was initially as described in Example 2, but after hydrolysis and dropwise addition of 170 ml of water the reaction mixture was cooled to 30° C. and the pH was brought to about 5.5, at from 30° to 40° C., by slow introduction of a 25% strength aqueous sodium hydroxide solution. After this pH had been reached, the reaction mixture was cooled to 20° C. and the product was then immediately filtered off with suction, washed with a water/ethanol (50:50 by volume) mixture and with ethanol, and dried under reduced pressure at 75° C.

The yield was 54.5 g, corresponding to 82.1% of theory.

Analysis: According to HPLC the product contained 9–11% of sodium riboflavin-4'-phosphate, 75–78% of sodium riboflavin-5'-phosphate and 5–6% of unconverted riboflavin.

Optical rotation: $+37.3 - +38°$
Sodium content: about 5%
pH of a 3% strength aqueous solution: 5–6.3.

EXAMPLE 4

A. 12 ml of phosphorous oxychloride were introduced into 100 ml of diethylene glycol dimethyl ether and 20 g (0.048 mol) of riboflavin potassium salt, as a fine powder, were added in portions, with stirring, whereupon the temperature rose to 30° C. The reaction mixture was then heated to 35° C. and stirred at this temperature for 3 hours. When the suspension had cooled to RT, the product was filtered off with suction, under N₂, washed with 100 ml of diethylene glycol dimethyl ether and dried. According to HPLC analysis, the product contained 91% of riboflavin-4',5'-phosphoric acid chloride and only 1% of unconverted riboflavin B. 200 ml of water were heated to 75°–85° C. and the product obtained under A. was introduced, in portions, into the water at this temperature. The reaction mixture was then stirred for a further 15 minutes at from 90° to 95° C. It was then cooled slowly and at 40° C. was brought to pH 5.5 by means of 25% strength aqueous sodium hydroxide solution. When the desired pH had been reached, the reaction mixture was cooled to 20° C. and the product was then immediately filtered off with suction, washed with a water/ethanol (50:50 by volume) mixture and with ethanol and dried under reduced pressure at 75° C. The yield was 19 g.

Analysis: According to HPLC, the product contained about 76% of riboflavin-5'-phosphate, about 9% of riboflavin4'-phosphate and about 5% of riboflavin.

We claim:

1. Riboflavin-4',5'-cyclophosphoric acid ester chloride of the formula I

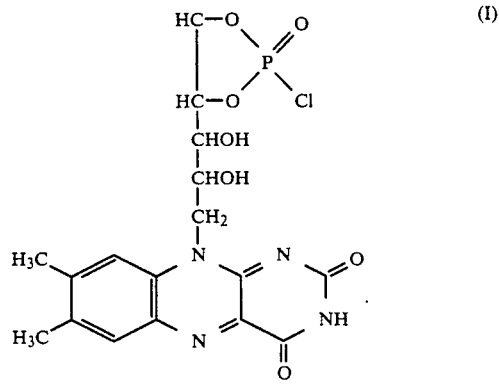

* * * * *